United States Patent [19]

Weetall

[11] 4,034,073

[45] July 5, 1977

[54] COMPOSITE FOR BIASED SOLID PHASE RADIOIMMUNOASSAY OF TRIIODOTHYRONINE AND THYROXINE

[75] Inventor: Howard H. Weetall, Big Flats, N.Y.

[73] Assignee: Corning Glass Works, Corning, N.Y.

[22] Filed: Mar. 28, 1975

[21] Appl. No.: 563,102

[52] U.S. Cl. .................................. 424/1; 23/230 B; 23/230.6; 424/12

[51] Int. Cl.$^2$ .................. G01N 33/00; G01N 33/16

[58] Field of Search .............. 424/1, 12; 252/301.1; 23/230 B, 230.6

[56] References Cited

UNITED STATES PATENTS

| | | | |
|---|---|---|---|
| 3,519,538 | 7/1970 | Messing et al. | 195/63 |
| 3,646,346 | 2/1972 | Catt | 424/12 X |
| 3,652,761 | 3/1972 | Weetall | 424/12 |
| 3,799,740 | 3/1974 | Mincey | 23/230 B |
| 3,904,373 | 9/1975 | Harper | 252/408 |

OTHER PUBLICATIONS

Weetall, Biochem. Journal, vol. 117, 1970, pp. 257–261.
Weetall, Biochimica et Biophysica Acta, vol. 212, No. 1, July 15, 1970, pp. 1–7.

Primary Examiner—Benjamin R. Padgett
Assistant Examiner—Christine M. Nucker
Attorney, Agent, or Firm—James A. Giblin; Clinton S. Janes, Jr.; Clarence R. Patty, Jr.

[57] ABSTRACT

Immunochemical composites consisting of saturating amounts of radio-labelled triiodothyronine ($T_3$) or thyroxine ($T_4$) complexed respectively to anti-$T_3$ or anti-$T_4$ antisera covalently coupled to suspendable porous glass particles via an intermediate silane coupling agent. The composites are pre-loaded into individual tubes used in solid phase radioimmunoassay of $T_3$ or $T_4$, requiring the addition of only test serum or standard, thereby minimizing chances of erroneous assay.

4 Claims, 3 Drawing Figures 4,034,073

COMPOSITE FOR BIASED SOLID PHASE RADIOIMMUNOASSAY OF TRIIODOTHYRONINE AND THYROXINE

BACKGROUND OF THE INVENTION

1. Field

This invention relates generally to the field of solid phase radioimmunoassay of $T_3$ or $T_4$, and specifically to reagents useful in such assays.

Radioimmunoassay (RIA) is a term used to describe any of several methods for determining very low concentrations of substances (especially in biological fluids), which methods are based on the use of radioactively labelled substances which can form immunochemical complexes. A typical RIA is based on the observation that a known amount of a radioactively labelled substance (against which there exists antibodies) will tend to compete with an unknown amount of that substance (unlabelled) for a limited number of complexing sites on the antibodies. Thus, such a RIA is performed by adding a known amount of labelled substance and a fluid containing an unknown amount of the substance (unlabelled) to a given amount of antibodies to the substance. During a suitable incubation period, complexes of both antibody-substance (unlabelled) and antibody-substance (labelled) are formed. These complexes are then separated from the reaction medium and radioactivity counts are taken of either the removed complexes or the remaining solution. These counts can be used to determine the unknown concentration by known means.

It can be appreciated that an essential step for such a RIA involves the separation of complexed products from the incubation medium. This separation step is greatly facilitated by using antibodies which have been attached to essentially water-insoluble carrier materials. The technique for the use of such materials has become known as solid phase radioimmunoassay or SPRIA. The present invention discloses novel reagents which can be used in the SPRIA of either $T_3$ or $T_4$.

2. Prior Art

To date, there are a wide variety of radioassay "kits" available commercially for determining concentrations of $T_3$, $T_4$, and/or combinations of those substances. See, for example, the recent directory listing "Radioassay Test Kits and Components", Laboratory Management, September, 1974, pages 29–42. Generally, the use of such kits is based on the affinity of $T_3$ or $T_4$ (labelled, for example, with $I^{125}$) for anti-$T_3$ or anti-$T_4$ antibodies. All such kits require a sequence of assay steps some of which are subject to operator error in preparation and/or measuring of the various reagents needed for a given test.

Although it can be appreciated that the use of SPRIA techniques can reduce some of the steps, such techniques still require separate steps for preparing or mixing the immobilized antibody, adding a precise amount of labelled material (tracer), adding an unknown sample, incubating, separating, and counting. Each of these steps is subject to operator error. It is an object of the present disclosure to provide a simplified SPRIA for $T_3$ and $T_4$ which requires less operator steps because of the novel reagents used. The method and reagents are disclosed in detail hereunder.

SUMMARY OF THE INVENTION

The reagents useful for a solid phase radioimmunoassay of $T_3$ or $T_4$ comprise immunochemical composites consisting of saturating amounts of radioactively labelled $T_3$ or $T_4$ complexed respectively to sub-composites of anti-$T_3$ or anti-$T_4$ antibodies covalently coupled via an intermediate silane coupling agent to suspendable porous glass particles having an average particle size ranging from about 0.7 to 4.0 microns. In very preferred embodiments, the composites are in an aqueous suspension contained in a unit tube for individual assays of $T_3$ or $T_4$ and the saturating amounts of $T_3$ or $T_4$ are labelled with $I^{125}$. Such tubes require the addition of only an unknown sample or a standard.

SPECIFIC EMBODIMENTS

Figure 1:
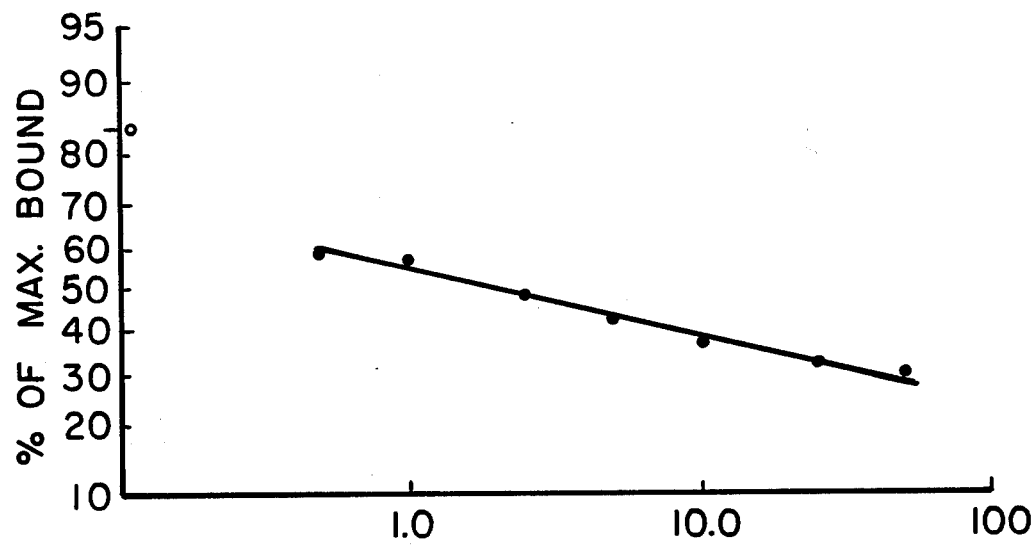
FIG. 1 is a graph illustrating the percent of maximum binding achieved with varying amounts of unlabelled $T_3$ added to one of the disclosed reagents.

The reagents of the present invention are useful in RIA's commonly referred to as biased assays. In biased radioassays, there occurs a displacement of one species of a substance (tagged or untagged) for the corresponding species (untagged or tagged). The amount of displacement can be related to the concentration of an unknown. Such an assay is commonly referred to as biased to distinguish it from other assays such as competitive binding assay (CBA) wherein there is an initial competition between tagged and untagged species of the same substance for available complexing sites on anti-substance antibodies.

A very important property of the present reagents is that they consist of immobilized anti-$T_3$ or anti-$T_4$ antibodies to which a maximum amount of labelled $T_3$ or $T_4$ respectively is complexed. The immobilized antibodies must be saturated with the respective tagged substance to assure the largest amount of displacement of the labelled species by the unlabelled species of unknown amount. Such a high displacement facilitates counting and sensitivity. As used herein, the expression saturating amount or its equivalent refers to an immobilized antibody composite to which a maximum amount of labelled $T_3$ or $T_4$ is complexed. In addition to being fully saturated with the corresponding tagged species, it is also important that the immobilized antibodies have a high degree of loading on the support material to maximize assay sensitivity. A high degree of loading of the antibodies per unit weight of total composite can be achieved by covalently coupling the antisera to high surface area porous glass particles having a particle size which permits them (and the resulting composite) to remain in aqueous suspension during the assay incubation periods. Such suspendability can be assured by using porous glass particles having an average pore size ranging from about 300A to 1000A and an average particle size ranging from 0.7 to 4 microns ($\mu$). Such porous glass particles can be prepared in accordance with the general teachings of United States patent application Ser. No. 447,250, filed on Mar. 1, 1974 in the names of F. Baker and D. Eaton, entitled "Suspendable Porous Glass Particles", and assigned to the present assignee.

The porous glass particles were silanized by known means and reacted with anti-$T_3$ and anti-$T_4$ antisera, respectively, to couple the antibodies to the glass surfaces via either azo linkage or through an amide using a N-hydroxysuccinamide derivative. Detailed descriptions of methods of coupling antibodies via an azo linkage to the surfaces of inorganics, especially porous glass, can be found in U.S. Pat. No. 3,652,761 issued to Weetall and United States patent application Ser. No. 447,252, filed Mar. 1, 1974 in the names of W. Vann and S. Yaverbaum, entitled "Solid Phase Radioimmunoassay", and assigned to the present assignee. In the above disclosures, it can be seen that a wide variety of antibodies can be coupled to porous blass via an intermediate silane coupling agent. The antibodies immobilized via the N-hydroxysuccinamide derivative (NHS-glass) were prepared as follows (approximately 10 grams): A 10 g portion of the porous glass particles (550A average pore diameter, 0.7 to 4.0 $\mu$average particle size) is silanized by known means to produce an alkylamine derivatized surface. To the alkylamine glass, 14 grams of powdered succinic anhydride are added. To the mixture is added 100 ml. of reagent grade chloroform and the container is swirled to disperse the anhydride. Then 20 ml. of triethylamine (TEA) is added in 4 increments spaced by 5 minutes. After the 4th addition of TEA, most of the anhydride dissolves and the pH should be lower than 7. The reactants are allowed to stand at room temperature overnight. The NHS-glass particles are entrifuged out and ready for antibody coupling. The anti-$T_3$ or anti-$T_4$ antibodies are coupled by first diluting 1 ml. of the appropriate serum to 8 ml. with 0.01 M phosphate buffer at pH 7.5 and then reacting the diluted serum with 1 gram of the NHS glass. The coupled antibodies are then centrifuged out and ready for subsequent reaction with $I^{125}$ $T_3$ or $I^{125}$ $T_4$ to saturate complexing sites on the respective coupled antibodies.

Hereinafter the immobilized antibodies are referred to as IMA ($T_3$) or IMA ($T_4$) as indicated. The IMA ($T_3$) or IMA ($T_4$) subcomposites were fully saturated with labelled $T_3$ or $T_4$, respectively by reacting an excess amount of $I^{125}$ $T_3$ or $I_{125}$ $T_4$ with the IMA's to fully saturate antibody complexing sites and then pouring off the reaction solutions to remove the excess labelled substance which had not complexed. The resulting composites are then washed with buffers, and resuspended in aqueous buffered solutions in individual test tubes. To perform SPRIA of either substance, it was then necessary to add only the unknown serum or a standard, allow for a suitable incubation time, centrifuge the complexed products, and count in a radioactivity counting device.

EXAMPLE I

Assay of Triiodothyronine ($T_3$) by Solid Phase Radioimmunoassay Using Antibodies To $T_3$ Coupled to Porous Glass Particles And Saturated With $I^{125}$ $T_3$ A small quantity (about 100 mg) of the IMA ($T_3$) consisting of anti-$T_3$ antibodies coupled to the NHS-glass was reacted with enough $I^{125}$ labelled $T_3$ (approximately 20,000 cpm) to give 10,000 cpm added per 0.1 ml. of the IMA ($T_3$) when suspended in individual tubes at its final dilution. This was then brought to 1.0 ml. with 0.01 M phosphate buffered saline (PBS), pH 7.4, containing 1% bovine serum albumin (BSA). The material was incubated for 2 hours at 37° C. with one vortex after 60 minutes, centrifuged at 3000 RPM, the supernatant discarded, and the residue washed once with buffer. The immobilized antibody having a saturating amount of $I^{125}$ $T_3$ complexed thereto was then dispensed into unit tubes by adding 50 $\mu$g of the composites to each of 18 tubes containing 0.7 ml. of buffer.

The pre-loaded unit tubes were stored for 24 hours at room temperature before assay. The following were added to each tube in the amounts indicated, the merthiolate being added to debind any $T_3$ complexed to serum proteins.

TABLE I

| Tube No. | $T_3$-free Human Serum | Merthiolate (10 mg/ml.) | Cold $T_3$ (ng/ml.) |
|---|---|---|---|
| 1 | 0.1 ml. | 0.1 ml. | 0.0 |
| 2 | 0.1 ml. | 0.1 ml. | 0.0 |
| 3 | 0.1 ml. | 0.1 ml. | 0.1 |
| 4 | 0.1 ml. | 0.1 ml. | 0.1 |
| 5 | 0.1 ml. | 0.1 ml. | 0.5 |
| 6 | 0.1 ml. | 0.1 ml. | 0.5 |
| 7 | 0.1 ml. | 0.1 ml. | 1.0 |
| 8 | 0.1 ml. | 0.1 ml. | 1.0 |
| 9 | 0.1 ml. | 0.1 ml. | 2.5 |
| 10 | 0.1 ml. | 0.1 ml. | 2.5 |
| 11 | 0.1 ml. | 0.1 ml. | 5.0 |
| 12 | 0.1 ml. | 0.1 ml. | 5.0 |
| 13 | 0.1 ml. | 0.1 ml. | 10.0 |
| 14 | 0.1 ml. | 0.1 ml. | 10.0 |
| 15 | 0.1 ml. | 0.1 ml. | 25.0 |
| 16 | 0.1 ml. | 0.1 ml. | 25.0 |
| 17 | 0.1 ml. | 0.1 ml. | 50.0 |
| 18 | 0.1 ml. | 0.1 ml. | 50.0 |

The tubes were incubated at 37° C. for 2 hours with a vortex after 60 minutes, centrifuged at 3000 RPM for 10 minutes, decanted into another tube, and both tubes were counted for radioactivity. A summary of the results is shown in FIG. 1 which shows the percent of maximum binding v. the amount of cold (unlabelled) $T_3$ added.

When the data of FIG. 1 is used to generate a displacement curve, it can be seen that a successful $T_3$ assay was accomplished in the clinically significant concentration range for $T_3$ using preloaded individual tubes already containing a saturating amount of $I^{125}$ labelled $T_3$.

EXAMPLE II

Solid Phase Radioimmunoassay of Thyroxine ($T_4$) Using Abtibodies to $T_4$ Coupled to Porous Glass Particles Saturated with $I^{125}$ $T_4$ The procedures used in Example I were used with the following differences:

A. The immobilized antibody was IMA ($T_4$), immobilized via azo linkage by known means using diazotized silanized glass.

B. The initial incubation period to load the IMA ($T_4$) with $I^{125}$ $T_4$ was 60 minutes at 37° C. with no vortexing. The following amounts of cold $T_4$ standards were used in buffer (not $T_4$-free serum):

0, 0.313, 0.95, 1.25, 1.88, 2.50, 3.75, and 5.00 ng/ml.

Figure 2:
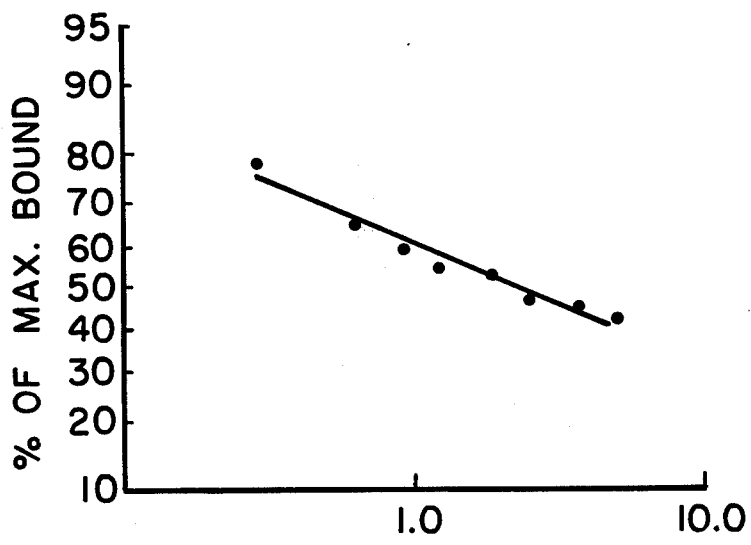
FIG. 2 is a graph illustrating a $T_4$ displacement curve generated using one of the disclosed reagents.

The results of this example are summarized in FIG. 2 which shows the percent of maximum $T_4$ bound v. amount of cold $T_4$ added (ng/ml.).

The data of FIG. 2 can be used to prepare a displacement curve indicating that a successful $T_4$ assay can be accomplished using the IMA ($T_4$) saturated with $I^{125}$ $T_4$.

EXAMPLE III

FURTHER ASSAYS OF T₄

Preparation of Individual Pre-Loaded Tubes

One gram of anti-T$_4$ antibody coupled by azo linkage to porous glass particles having an average particle size of about 1 micron was incubated with enough I$^{125}$ labelled T$_4$ to completely saturate all antibody complexing sites. The incubation was for 2 hours in 0.5% BSA, 0.03 M PBS, pH 7.2. The resulting preparation was then cnetrifuged and washed in the buffer to remove excess I$^{125}$ T$_4$. It was determined that the IMA (T$_4$) concentration necessary for displacement studies, 12,000 cpm, was present in each unit tube that the IMA (T$_4$) was placed in. The wash products were then resuspended in enough 0.01 MPBS, pH 7.4, containing 1% BSA such that 0.7 ml. of the suspension would give a count of 10,000 cpm.

Individual unit tubes were prepared by pipetting 0.7 ml. of the IMA (T$_4$) I$^{125}$ T$_4$ suspension into tubes containing the abovedescribed buffer. The tubes were stoppered and stored at 4° C.

Displacement Curves

Figure 3:
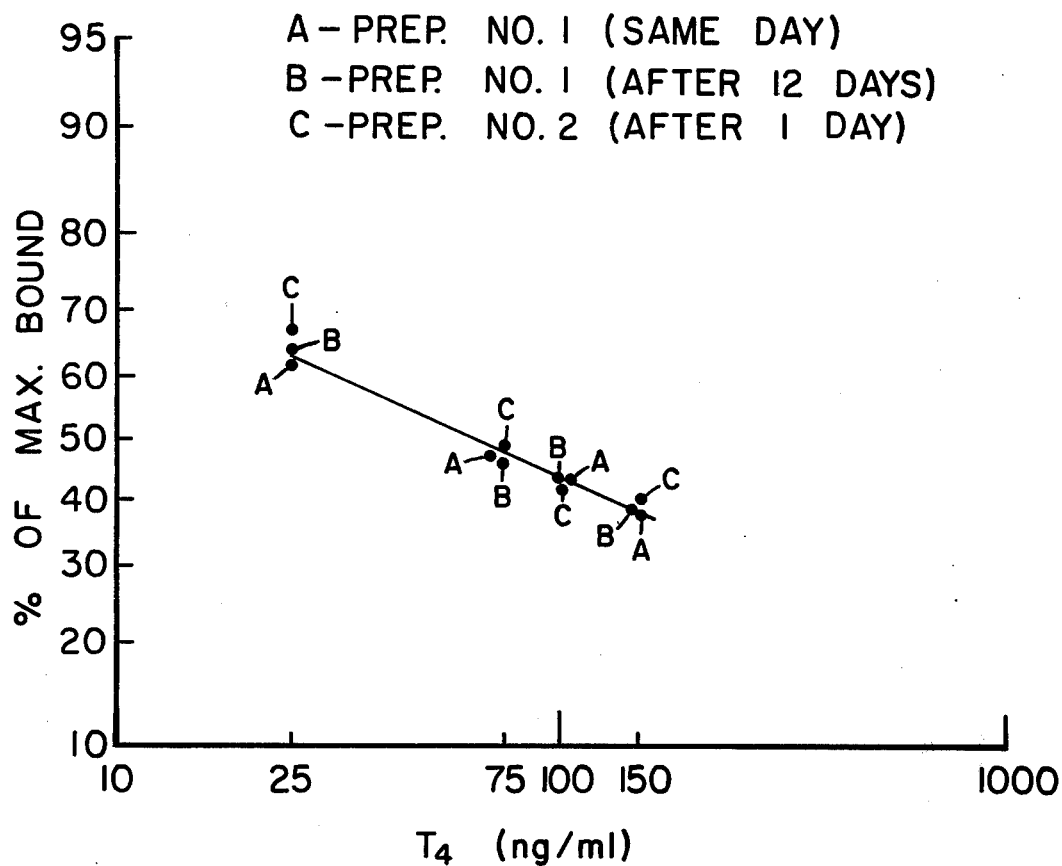
FIG. 3 is a graph illustrating $T_4$ displacement curves generated using the disclosed reagents on the day of preparation, after one day, and after twelve days.

To each unit tube, already containing the label complexed to the IMA (T$_4$) was added 0.05 ml. of T$_4$-free serum and 0.05 ml. of T$_4$ standards containing 0, 25, 75, 100, or 150 ng/ml. The merthiolate (1.0 mg/tube) can be included in the preparations. The reactants were incubated for two hours at 37° C. with vortexing at the end of one hour. The samples were then centrifuged at 4000 RPM and the supernatants counted. The initial binding percent (B$_o$) was 65% of the preparation. In the absence of "T$_4$-free serum", this value exceeds 80%. Results of these studies are shown in FIG. 3 which shows excellent reproducability in three curces. FIG. 3 shows the displacement curves generated with two separate samples and a third curve generated by sample No. 1 after 12 days storage at room temperature.

COMPARISON EXAMPLES

The composites of the above examples (T$_4$ assays) were used to determine T$_4$ concentrations of human serum samples obtained from a local hospital and for which T$_4$ concentration had been determined by competitive protein binding techniques (CPB). The results are compared in Table II, where composite samples of both the azo and NHS coupled antibodies were suspended in individual unit tubes and used to determine T$_4$ concentrations of 25 λ serum samples.

TABLE II

| | Comparison Assays for T$_4$ | | |
| | | Via Disclosed Composites | |
| Sample No. | Via CPB | Azo-Coupled Anti-T$_4$ IMA | NHS-Coupled Anti-T$_4$ IMA |
| --- | --- | --- | --- |
| 1 | 60 | 105 | 85 |
| 2 | 132 | 170 | 140 |
| 3 | 64 | 96 | 100 |
| 4 | 84 | 115 | 125 |
| 5 | 12 | 14 | 11 |
| 6 | 78 | 105 | 110 |
| 7 | 84 | 105 | 90 |
| 8 | 60 | 96 | 85 |
| 9 | 74 | 110 | 90 |
| 10 | 108 | 115 | 102 |
| 11 | 98 | 115 | 95 |
| 15 | 84 | 96 | 95 |

I claim:

1. A reagent useful for a solid phase radioimmunoassay of triiodothyronine comprising an aqueous suspension of an immunochemical composite consisting of a saturating amount of radioactively labelled triiodothyronine complexed to a sub-composite consisting of anti-triiodothyronine antibodies covalently coupled via an intermediate silane coupling agent to suspenable particles of porous glass.

2. The reagent of claim 1 wherein the porous glass particles of the suspension have an average pore diameter ranging from 300A to 1000A and an average particle size ranging from 0.7 $\mu$ to 4 $\mu$ and the triiodothyronine is labelled with I$^{125}$.

3. A reagent useful for a solid phase radioimmunoassay of thyroxine comprising an aqueous suspension of an immunochemical composite consisting of a saturating amount of radioactively labelled thyroxine complexed to a sub-composite consisting of anti-thyroxine antibodies covalently coupled via an intermediate silane coupling agent to suspendable particles of porous glass.

4. The reagent of claim 3 wherein the porous glass particles of the suspension have an average pore diameter ranging from 300A to 1000Å and an average particle size ranging from 0.7 $\mu$ to 4 $\mu$ and the thyroxine is labelled with I$^{125}$.

* * * * *